(12) United States Patent
Ennis

(10) Patent No.: US 6,962,790 B1
(45) Date of Patent: Nov. 8, 2005

(54) PREDICTIVE ASSAY FOR IMMUNE RESPONSE

(75) Inventor: Francis A. Ennis, Shrewsbury, MA (US)

(73) Assignee: University of Massachusetts Medical Center, Worcester, MA (US)

(*) Notice: Subject to any disclaimer, the term of this patent is extended or adjusted under 35 U.S.C. 154(b) by 0 days.

(21) Appl. No.: 09/159,172

(22) Filed: Sep. 23, 1998

(51) Int. Cl.$^7$ ............................................. C12N 15/00
(52) U.S. Cl. .................... 435/7.24; 424/9.2; 424/199.1; 424/200.1; 435/6
(58) Field of Search .............................. 424/9.2, 199.1, 424/200.1; 435/7.24, 6

(56) References Cited

U.S. PATENT DOCUMENTS

| | | | | |
|---|---|---|---|---|
| 5,200,320 | A | * | 4/1993 | Sette et al. ................. 435/7.24 |
| 5,674,502 | A | | 10/1997 | Ennis ....................... 424/206.1 |
| 5,750,356 | A | | 5/1998 | Spack et al. ............... 435/7.24 |
| 5,763,284 | A | | 6/1998 | Tal et al. ...................... 436/501 |
| 5,766,601 | A | | 6/1998 | Ennis ....................... 424/206.1 |
| 5,962,318 | A | | 10/1999 | Rooney et al. .............. 435/325 |
| 6,627,407 | B2 | * | 9/2003 | Ennis ......................... 435/7.24 |

FOREIGN PATENT DOCUMENTS

WO    WO 94/22917    10/1994

OTHER PUBLICATIONS

Sette et al, Nature, 328, 395–399, 1987.*
Baier et al, Journal of Virology, 69, 2357–2365, 1995.*
Gotch et al, Journal of Experimental Medicine, 165, 408–416, 1987.*
McMichael et al, Journal of General Virology, 67, 719–726, 1986.*
Wisdom, *Peptide Antigens, A Practical Approach*, Oxford University Press, 1994, Chapters 1, 4 and 7.*
Zegers et al, *Immunological Recognition of Peptides in Medicine and Biology*, CRC Press, 1995. Chapter 8.*
Reitan, L.J. and Secombes, C.J., "In Vitro Methods for Vaccine Evaluation," *Dev. Biol. Stand.* 90:293–301 (1997).
Lein, A.D. and von Reyn, C.F., "In Vitro Cellular and Cytokine Responses to Mycobacterial Antigens: Application to Diagnosis of Tuberculosis Infection and Assessment of Response to Mycobacterial Vaccines," *The American Journal of the Medical Sciences*, 313(6):364–371 (1997).
Smith, G.L., et al., "Synthesis and Cellular Location of the Ten Influenza Polypeptides Individually Expressed by Recombinant Vaccinia Viruses," *Virology* 160:336–345 (1987).
Böyum, A., "Isolation of Mononuclear Cells and Granulocytes from Human Blood," Scand. J. Clin. Lab. Invest. 21 (Suppl. 97):77–89 (1968).

Kurane, I., et al., "Dengue Virus–Specific Human T Cell Clones, Serotype Crossreactive Proliferation, Interferon γ Production, and Cytotoxic Activity," *J. Exp. Med.* 170:763–775 (1989).
Fathman, C.G., et al., "Long–Term Culture of Immunocompetent Cells," in Paul, ed., *Fundamental Immunology*, 2nd Ed., New York: Raven Press, Chapter 30:803–815 (1989).
Green, S., et al., "Dengue Virus–Specific Human CD4$^+$ T–Lymphocyte Responses in a Recipient of an Experimental Live–Attenuated Dengue Virus Type 1 Vaccine: Bulk Culture Proliferation, Clonal Analysis, and Precursor Frequency Determination," *J. Virol.* 67(10):5962–5967 (1993).
Littaua, R.A., et al., "An HLA–C Restricted CD8$^+$ Cytotoxic T–Lymphocyte Clone Recognizes a Highly Conserved Epitope on Human Immunodeficiency Virus Type 1 gag," *J. Virol.* 65(8):4051–4056 (1991).
Kuwano, K., et al., "Cross–Reactive Protection Against Influenza A Virus Infections by an NS1–Specific CTL Clone," *Virology* 178:174–179 (1990).
Kuwano, K., et al., "HA2 Subunit of Influenza A H1 and H2 Subtype Viruses Induces a Protective Cross–Reactive Cytotoxic T Lymphocyte Response," *J. of Immunology* 140(4):1264–1268 (1988).
Jameson, J., et al., "Human Cytotoxic T–Lymphocyte Repertoire to Influenza A Viruses," *J. Virol.* 72(11) :8682–8689 (1998).
Claassen, I. and Osterhaus, A., "The iscom structure as an immune–enhancing moiety: experience with viral systems," *Res. Immunol.* 143(5):531–541 (1992).

\* cited by examiner

*Primary Examiner*—David Saunders
(74) *Attorney, Agent, or Firm*—Hamilton, Brook, Smith & Reynolds, P.C.

(57) ABSTRACT

The present invention relates to an in vitro method for determining the ability of a vaccine composition which comprises one or more antigens or a nucleic acid molecule which encodes one or more antigens to stimulate a T cell response. In one embodiment, the method comprises the steps of: (1) contacting antigen presenting cells in culture with a vaccine composition selected from among the group of vaccine compositions, thereby, if one or more of the antigens or nucleic acid molecules can be taken up and processed by the antigen presenting cells, producing one or more processed antigens; (2) contacting the antigen presenting cells with T cells under conditions sufficient for the T cells to respond to one or more of the processed antigens; (3) determining whether the T cells respond to one or more of the processed antigens; whereby if the T cells respond to one or more of the processed antigens, then the vaccine composition stimulates a T cell response; and (4) repeating steps (1), (2) and (3) with each vaccine composition in the group, thereby identifying vaccine compositions which stimulate a T cell response; and, if one or more of the vaccine compositions stimulates a T cell response, (5) selecting at least one vaccine composition which stimulates a T cell response for assessment in one or more animals and/or human subjects.

21 Claims, 2 Drawing Sheets

PREDICTIVE ASSAY FOR IMMUNE RESPONSE

BACKGROUND OF THE INVENTION

Among the greatest successes in the field of public health is widespread vaccination against a variety of formerly common infectious diseases. For example, public vaccination programs in the United States have eradicated smallpox and dramatically reduced the incidence of diseases such as measles, rubella, polio and diphtheria, among others. However, the development of novel vaccine compositions is still an active area of research. In particular, the development of effective vaccines for a number of diseases for which no clinically proven vaccine exists remains an important goal. For example, a vaccine which protects against infection by human immunodeficiency virus (HIV) is a primary goal in efforts to control the spread of AIDS. Also needed are vaccine compositions which have improved efficacy in comparison to vaccines in current use.

The efficacy of a vaccine for use in humans depends upon the ability of the vaccine formulation to elicit an immune response which is sufficient to provide protection against subsequent challenge with the pathogen. Experimental vaccines are typically evaluated first in vivo in small animals, such as mice, guinea pigs or rabbits. The assessment of the experimental vaccines generally relies upon measurements of serum antibody responses and, sometimes, antigen-specific lymphocyte proliferative responses. Vaccine formulations which are successful in these animal models are then tested in sub-human primates and, finally, in humans.

The assessment of a test vaccine in an animal model is costly and takes considerable time. Typically, several doses of vaccine are administered to the animal at intervals of several weeks. The immune response of primates to a given test vaccines is often less than that of smaller animals, and clinical studies in humans ultimately required to determine the efficacy of a test vaccine. In addition to the large cost associated with purchasing and housing animals for long periods of time, each step of the process requires a minimum of several months. Thus, the number of experimental vaccines which can be evaluated using prior art methods is necessarily limited, with the possible result that potentially useful vaccine formulations may never be tested.

There is, therefore, a need for an in vitro test for determining the human immune response to an experimental vaccine construct which would allow the rapid evaluation of large numbers of candidate vaccine compositions within a short time period and at reasonable cost.

SUMMARY OF THE INVENTION

The present invention relates to a method for assessing the ability of a candidate vaccine composition to stimulate a T cell response. In one embodiment, the invention provides a method for selecting one or more vaccine compositions from among a group of vaccine compositions for in vivo assessment, for example, in one or more animal or human subjects. Each of the vaccine compositions comprises one or more antigens or one or more nucleic acid molecules encoding one or more antigens. The method comprises the steps of: (1) contacting antigen presenting cells in culture with a vaccine composition selected from among the group of vaccine compositions, thereby, if one or more of the antigens or nucleic acid molecules can be taken up and processed by the antigen presenting cells, producing one or more processed antigens; (2) contacting the antigen presenting cells with T cells under conditions sufficient for the T cells to respond to one or more of the processed antigens; (3) determining whether the T cells respond to one or more of the processed antigens; whereby if the T cells respond to one or more of the processed antigens, then the vaccine composition stimulates a T cell response; and (4) repeating steps (1), (2) and (3) with each additional vaccine composition in the group, thereby identifying the vaccine compositions within the group which stimulate a T cell response; and, if one or more of these vaccine compositions stimulates a T cell response, (5) selecting at least one vaccine composition which stimulates a T cell response for assessment in one or more animals and/or in one or more human subjects.

In another embodiment, the invention relates to a method of selecting a vaccine composition from a group consisting of two or more vaccine compositions for assessment in one or more animals or in one or more human subjects. Each of the vaccine compositions comprises one or more antigens or one or more nucleic acid molecules encoding one or more antigens. The method comprises the steps of: (1) contacting antigen presenting cells in culture with a vaccine composition selected from among said group of vaccine compositions, thereby, if one or more of the antigens or nucleic acid molecules are taken up and processed by the antigen presenting cells, producing one or more processed antigens; (2) contacting the antigen presenting cells with T cells under conditions sufficient to produce a T cell response to one or more of the processed antigens, thereby producing a vaccine composition-stimulated T cell response; (3) measuring the vaccine composition-stimulated T cell response; (4) repeating steps (1), (2) and (3) with each of the remaining vaccine compositions in the group, thereby identifying the vaccine composition or compositions which stimulate the greatest T cell response; (5) selecting the vaccine composition or compositions which stimulate the greatest T cell response for assessment in one or more animals and/or in one or more human subjects.

In a further embodiment, the invention relates to a method for assessing the ability of a vaccine composition comprising one or more antigens or one or more nucleic acid molecules encoding one or more antigens to stimulate a protective T cell response. The method comprises the steps of: (1) contacting human antigen presenting cells in culture with the vaccine composition, thereby, if one or more of the antigens or nucleic acid molecules can be taken up and processed by the antigen presenting cells, producing one or more processed antigens; (2) contacting the antigen presenting cells with human T cells under conditions sufficient to produce a T cell response to one or more of the processed antigens, thereby producing a T cell response; (3) measuring the T cell response; and, if the T cell response is greater than a pre-selected value, (4) assessing the ability of the vaccine composition to stimulate a protective T cell response in one or more animals or in one or more human subjects.

In another embodiment, the method of the invention comprises the steps of: (1) contacting human antigen presenting cells in culture with the vaccine composition, whereby, if one or more of the antigens are taken up and processed by the antigen presenting cells, said antigen or antigens are processed by the antigen presenting cells, thereby producing one or more processed antigens; (2) contacting the antigen presenting cells of step (1) with human T cell clones which are specific for an epitope within one or more of the antigens for a period of time sufficient for the human T cell clones to respond to one or more of the processed antigens; and (3) determining whether the human T cell clones respond to the processed antigen or antigens.

If the T cell clones respond to the processed antigen or antigens, the method can, optionally, further include the step of assessing the vaccine composition in one or more animals or human subjects.

Preferably, the vaccine composition includes at least one antigen which comprises a T cell epitope, and the T cells are T cell clones which are specific for a T cell epitope in at least one of the antigens. In one embodiment, the T cells are $CD8^+$ T cells and the vaccine composition includes at least one antigen comprising a CD8 epitope. In this embodiment, the T cell response to the processed antigen can be, for example, T cell proliferation, cytolysis of the antigen presenting cells or the production of one or more cytokines.

In another embodiment, the T cells are $CD4^+$ T cells and the vaccine composition includes at least one antigen which comprises a CD4 epitope. In this embodiment, the T cell response to the processed antigen which is determined can be, for example, T cell proliferation, stimulation of antibody production by B cells or production of one or more cytokines.

The present invention offers several advantages over prior art methods of evaluating candidate vaccine compositions. For example, the method of the invention can be completed in a relatively short time period. The present method can also be used as a first screen to determine which candidate compositions should be evaluated in much more expensive and time consuming in vivo tests. Thus, the method of the invention enables the efficient and cost effective evaluation of large numbers of potential vaccine compositions, increasing the possibility that effective vaccine compositions will be discovered.

DETAILED DESCRIPTION OF THE INVENTION

Figure 1A:
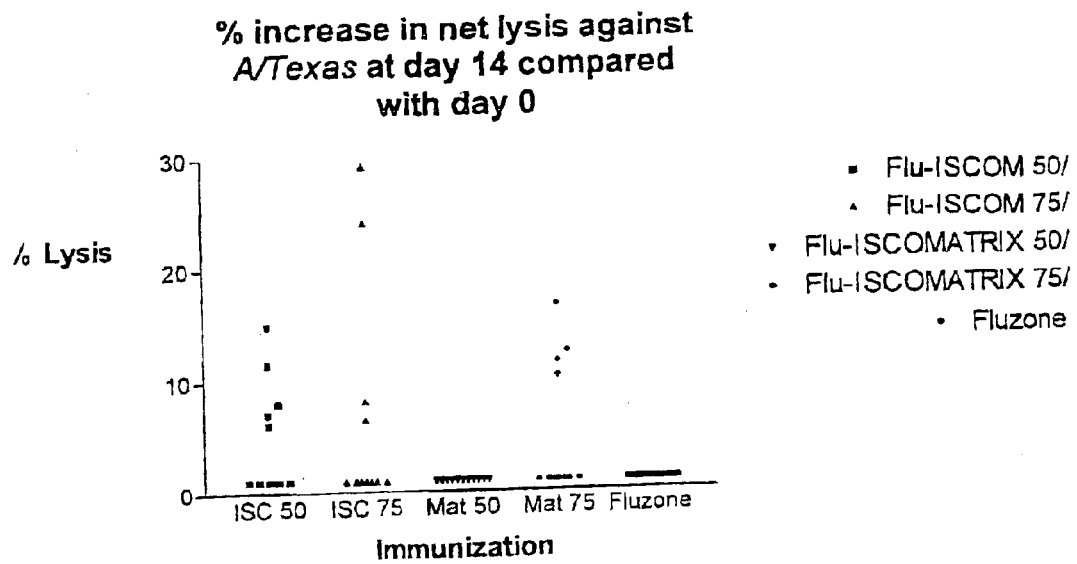
FIG. 1A is a graph showing the increase in percent lysis against influenza virus strain A/Texas compared to day 0 for several fluzone formulations at day 14.

Successful vaccines deliver to a host one or more antigens derived from a pathogen, thereby stimulating an immune response which protects against subsequent challenge with the pathogen. Such vaccines can take a variety of forms, including attenuated or killed pathogens, for example, viruses or bacteria; one or more proteins or peptides derived from a pathogen or synthetic or recombinant versions of such proteins or peptides; or one or more nucleic acid molecules encoding one or more proteins or peptides from the pathogen, such as a naked DNA vaccine or a nucleic acid molecule administered in a suitable vector, such as a recombinant virus or bacterium or an immunostimulating complex. Vaccines against cell proliferative diseases, such as cancers, typically utilize proteins or fragments thereof, or nucleic acid molecules encoding proteins or fragments thereof, which are unique to diseased cells or generally more abundant in diseased cells compared to healthy cells.

Cell-mediated immunity is dependent upon lymphocytes known as B cells and T cells. B cells produce antibodies targeted against extracellular antigens. T cells recognize antigen fragments (peptides) which are displayed at the surface of a host cell. Such antigen fragments result from uptake of the antigen by a host cell, or synthesis of the antigen within the host cell, followed by cleavage of the antigen within the cell. Although it is probable that most successful vaccines elicit both T cell and B cell responses, current methods for evaluating test vaccines generally focus on antibody production by B cells, and do not assess the ability of the test vaccine to elicit a T cell response.

Foreign proteins which are synthesized within the host cell or are taken up by the host cell via specific receptors are fragmented within the cytosol of the cell. One or more of the resulting peptides can become associated with class I major histocompatibility molecules (MHC I), and the resulting complexes are then presented at the surface of the cell. These MHC I/peptide complexes are recognized by specific T cell receptors in certain $CD8^+$ T cells, and the peptides so presented are referred to as CD8 epitopes.

A foreign protein can be taken up by a host cell nonspecifically via endocytosis and then fragmented into peptides in a cellular lysosomal or endosomal compartment. One or more of these peptides can then become associated with a class II major histocompatibility molecule (MHC II) to form a complex which is then presented at the surface of the host cell. These MHC II/peptide complexes are recognized by $CD4^+$ T cells expressing a specific receptor which recognizes the MHC II/peptide complex. These peptides are referred to as CD4 epitopes.

Peripheral T cells in the blood and organs of the immune system (e.g. spleen and lymph nodes) exist in a quiescent or resting state. Upon interaction of T cells with an MHC/epitope complex, the T cells proliferate and differentiate into activated cells having a variety of functions. $CD8^+$ T cells typically become cytotoxic upon activation and destroy antigen-presenting cells via direct contact. Activated $CD4^+$ T cells provide a helper function to B cells, enabling B cells to differentiate into antibody-producing cells. Activated $CD8^+$ T cells and $CD4^+$ T cells release a variety of cytokines (lymphokines or interleukins), which can, for example, control differentiation of many classes of lympholytic precursor cells.

In one embodiment, the invention provides a method for selecting one or more vaccine compositions from among a group of two or more vaccine compositions for in vivo assessment in one or more animals and/or human subjects. Each of the vaccine compositions comprises one or more antigens or one or more nucleic acid molecules encoding one or more antigens. The method comprises the steps of: (1) contacting antigen presenting cells in culture with a vaccine composition selected from among said group of vaccine compositions, thereby, if one or more of the antigens or nucleic acid molecules are taken up and processed by the antigen presenting cells, producing one or more processed antigens; (2) contacting the antigen presenting cells with T cells under conditions sufficient for the T cells to respond to one or more of the processed antigens; (3) determining whether the T cells respond to one or more of the processed antigens; whereby if the T cells respond to one or more of the processed antigens, then the vaccine composition stimulates a T cell response; and (4) repeating steps (1), (2) and (3) with each vaccine composition in the group, thereby identifying vaccine compositions which stimulate a T cell response; and, if one or more of the vaccine compositions stimulates a T cell response, (5) selecting at least one vaccine composition which stimulates a T cell response for assessment in vivo.

In another embodiment, the invention relates to a method of selecting at least one vaccine composition from a group consisting of two or more vaccine compositions for assessment in one or more animals and/or human subjects. Each of the vaccine compositions comprises one or more antigens or one or more nucleic acid molecules encoding one or more antigens. The method comprises the steps of: (1) contacting antigen presenting cells in culture with a vaccine composition selected from among said group of vaccine compositions, thereby, if one or more of the antigens or nucleic acid molecules can be taken up and processed by the antigen presenting cells, producing one or more processed antigens; (2) contacting the antigen presenting cells with T cells under conditions sufficient to produce a T cell response to one or more of the processed antigens, thereby producing a vaccine composition-stimulated T cell response; (3) measuring the vaccine composition-stimulated T cell response; (4) repeating steps (1), (2) and (3) with each of the remaining vaccine compositions in the group, thereby identifying one or more vaccine compositions which stimulate the greatest T cell response; and (5) selecting the vaccine composition or compositions which stimulate the greatest T cell response for assessment in an animal or in a human. In another embodiment, one or more of the vaccine compositions producing a stimulated T cell response greater than a pre-selected value are selected for in vivo assessment. Alternatively, one or more vaccine compositions having relatively high activity compared to the remaining vaccine compositions are selected for in vivo assessment.

In a further embodiment, the invention relates to a method for assessing the ability of a vaccine composition comprising one or more antigens or one or more nucleic acid molecules encoding one or more antigens to stimulate a protective T cell response. The method comprises the steps of: (1) contacting human antigen presenting cells in culture with the vaccine composition, thereby, if one or more of the antigens or nucleic acid molecules can be taken up and processed by the antigen presenting cells, producing one or more processed antigens; (2) contacting the antigen presenting cells with human T cells under conditions sufficient to produce a T cell response to one or more of the processed antigens, thereby producing a T cell response; (3) measuring the T cell response; and, if the T cell response is greater than a pre-selected value, (4) assessing the ability of the vaccine composition to stimulate a protective T cell response in one or more animals, human subjects or a combination thereof. The pre-selected value of the T cell response is, typically, chosen to represent a vaccine composition which is particularly active in stimulating a T cell response.

In another embodiment, the method of the invention comprises the steps of: (1) contacting human antigen presenting cells in culture with the vaccine composition, whereby, if one or more of the antigens are taken up and processed by the antigen presenting cells, said antigen or antigens are processed by the antigen presenting cells, thereby producing one or more processed antigens; (2) contacting the antigen presenting cells of step (1) with human T cell clones which are specific for an epitope within one or more of the antigens for a period of time sufficient for the human T cell clones to respond to one or more of the processed antigens; and (3) determining whether the human T cell clones respond to the processed antigen or antigens. If the T cell clones respond to the processed antigen or antigens, the method can, optionally, further include the step of assessing the vaccine composition in an animal or in a human.

A "processed antigen", as the term is used herein, refers to one or more epitopes derived from an antigen which are presented at the surface of an antigen presenting cell in combination with MHC I or MHC II.

The present method assesses the ability of a candidate vaccine composition to provide in vitro an antigen to antigen presenting cells in a manner which leads to processing and presentation of one or more T cell epitopes at the surface of the antigen presenting cells in combination with MHC I or MHC II. This in vitro determination provides an efficient screen for selecting compositions for more time-consuming in vivo testing in animals or in humans. This in vivo testing can be performed using methods which are well known in the art. For example, the vaccine composition can be administered to an animal or a human, and the ability of the induced immune response, if any, to protect against subsequent challenge from the pathogen from which the antigen or antigens are derived can be determined. Alternatively, or in conjunction with such a determination, the ability of the vaccine composition to induce in vivo the proliferation of T cells and/or antibodies which recognize one or more of the antigens can also be determined. Animals which can be used for in vivo testing include laboratory animals, domesticated animals and wild animals. Suitable examples include rodents, such as mice, hamsters, rats, guinea pigs and rabbits; primates, such as monkeys and apes; and domestic animals, such as dogs, cats, horses, chickens, cows and pigs.

The antigen presenting cells are contacted with the vaccine composition in cell culture in a suitable culture medium, as is known in the art, and under suitable conditions, such as physiological pH, and at a temperature from about room temperature to about physiological temperature, for a sufficient period of time for uptake and processing of the antigen by the antigen presenting cells. If the vaccine comprises a nucleic acid molecule, the antigen presenting cells are contacted with the vaccine composition for a sufficient amount of time for the antigen presenting cells to take up and express the nucleic acid molecule and process the resulting antigen. Generally, the antigen presenting cells are contacted with the vaccine composition for a period of several hours, for example, from about 2 to about 12 hours. Following contact with the vaccine composition, the antigen presenting cells are contacted with the T cells for a sufficient period of time for activation of the T cells and generation of a T cell effector response. Generally, this process requires several hours, for example, from about 2 to about 12 hours. Preferably, the APCs are contacted with the vaccine composition for a sufficient period time for antigen or nucleic acid molecule uptake, and then washed and placed in fresh media prior to addition of the T cells. Alternatively, the antigen presenting cells can be contacted with the vaccine composition and the T cells simultaneously or within a relatively short time interval. In this embodiment, the antigen presenting cells are contacted with the vaccine composition and the T cells for a sufficient amount of time for antigen processing and generation of a T cell response. Typically, such a process requires from about 4 to about 24 hours.

The vaccine composition, preferably, comprises at least one antigen, or a nucleic acid encoding at least one antigen, which is a protein or a peptide which comprises one or more T cell epitopes, such as one or more $CD8^+$ T cell epitopes, one or more $CD4^+$ T cell epitopes or a combination thereof. Preferably, the T cells are specific for a particular epitope present within the antigen. More preferably, the T cells are T cell clones derived from a single precursor T cell. In a particularly preferred embodiment, the T cells are human T cell clones.

In one embodiment, the epitope is a CD4+ T cell epitope and the T cells are CD4+ T cells. As discussed above, the effector functions of CD4+ T cells include releasing cytokines and stimulating B cells to become antibody-producing cells. Thus, in this embodiment, the extent of the T cell response to the antigen presenting cells can be determined by measuring T cell proliferation, the production of one or more cytokines or the stimulation of antibody production by B cells. Greater levels of T cell proliferation, antibody production or cytokine production would be expected to correlate with greater immunogenicity and potential efficacy of the vaccine composition.

In another embodiment, the epitope is a CD8 epitope and the T cells are CD8+ T cells. As discussed above, the effector functions of CD8+ T cells include lysis of antigen presenting cells and release of cytokines. Therefore, the extent of CD8+ T cell response to the antigen presenting cells can be determined using an assay for cell lysis or by measuring the production of one or more cytokines. The CD8+ T cell response can also be measured by measuring the extent of release of one or more cytokines. In general, it is expected that greater cell lysis activity or cytokine release will correlate with greater immunogenicity.

The antigen presenting cells can be selected from among any suitable cells which are potentially capable of taking up the antigen, such as a natural, purified or recombinant protein, or a nucleic acid molecule encoding the antigen, and presenting a peptide epitope derived from the antigen at the cell surface in combination with MHC I or MHC II. For example, when the epitope is a CD4 epitope, cells expressing MHC II molecules can be used. Such cells include macrophages, dendritic cells and B cells. When the epitope is a CD8+ T cell epitope, the antigen presenting cells can be selected from among any cells which express MHC I. In preferred embodiments, the antigen-presenting cells are professional antigen-presenting cells, such as macrophages, dendritic cells and B cells. The antigen presenting cells can be, for example, recombinant cells expressing heterologous MHC molecules. In a preferred embodiment, the antigen presenting cells are human cells. The antigen presenting cells present the proper MHC molecules and are, preferably, at least partially HLA matched with the T cells. More preferably, the APCs are autologous cells, that is, cells derived from the same donor as the T cells.

In one embodiment, the T cells are clones which are specific for a particular epitope, and the vaccine composition includes at least one antigen which comprises the epitope or at least one nucleic acid molecule encoding at least one antigen which comprises the epitope. In this embodiment, response of the epitope-specific T cell clones to antigen-presenting cells which have been contacted with the experimental vaccine composition indicates that the vaccine composition is able to effect the presentation of the epitope on the surface of the antigen-presenting cells in combination with an MHC I or MHC II molecule.

Epitope-specific T cell clones can be generated using methods which are generally known in the art (see, for example, Fathman, et al., in Paul, ed., *Fundamental Immunology*, second edition, Raven Press (1989), Chapter 30, the contents of which are hereby incorporated by reference in their entirety). The isolation of epitope-specific T cell clones is based on T cell biology. Generally, an animal, such as a mouse, is immunized with a preparation of antigens (a bacterial lysate, or a purified protein) or is infected with a virus, such as a wild type virus or a recombinant virus containing heterologous genes encoding one or more proteins from a pathogenic microorganism, such as a virus. The animal is then sacrificed and the peripheral blood mononuclear cells (PBMC: includes T cells, B cells, monocytes), spleen and lymph nodes are isolated. The isolated cells are then cultured in media containing a defined component of the original antigenic preparation, often a recombinant or purified protein, and the essential T cell growth factor interleukin-2 (IL-2). The only T cells which will proliferate are those which recognize MHC/epitope complex in which the epitope is derived from the antigenic preparation. These cells become activated and proliferate while the unactivated cells begin to die. The cultures are maintained for several weeks, with the media containing antigen and IL-2 being periodically replaced. Eventually, clusters of living and dividing cells (a T cell line) can be observed in some of the cultures.

The proliferating cells are generally not clonal at this point and are of limited use for assaying epitope specific T cell responses. The T cell line is, preferably, cloned through a process referred to as limiting dilution. In this method, PBMC are isolated from, for example, a mouse of the same strain as the original mouse used to isolate the T cell line. These cells, called antigen presenting cells, will serve as a source of MHC proteins and will present the MHC:peptide complex to the T cell line. The T cell line is diluted to a concentration of about 1 to 5 T cells/mL in a suspension of APCs that contains the antigen of interest and IL-2. This suspension is then transferred into, for example, round or "v"-bottom 96 well microtitre plates, so that each well contains, on average, no more than 1 T cell. The cultures are maintained for several weeks and a clone can grow out of one or more cultures.

The cells isolated by limiting dilution are the progeny of a single cell that expresses only one T cell receptor, and the clone is thus epitope-specific. However, in a situation in which the cloning procedure uses whole proteins or viruses, a single protein may contain many epitopes and the precise epitope will remain unknown. The epitope can be identified using a collection of overlapping synthetic peptides that span the entire amino acid sequence of the antigenic protein. These peptides can be used to stimulate proliferation or cytokine secretion in a direct stimulation assay, or they may be used as competitive inhibitors to block activation of the T cell clone by the antigenic protein.

Human T cell clones can also be isolated. Generally, these clones are isolated from individuals who have had an infection, for example, influenza, HIV or Dengue, or have been exposed to antigens in nature or by injection and have T cells that specifically respond to those antigens. These antigens are called "recall antigens" and include tetanus toxoid and *Candida albicans* extract. Human T cell clones are isolated from the PBMC.

The T-cell response to APCs treated with the test vaccine composition can be determined using a variety of assays which are known in the art. Several examples are taught by Fathman, et al., supra. For example, T cell proliferation can be measured using methods known in the art. In one embodiment, the epitope-specific T cells are mixed with irradiated antigen presenting cells and the test vaccine composition and cultured. The cells are cultured for a period of a few days to allow presentation of the epitope by the APCs and activation of the T cells. T cell proliferation is then assessed by monitoring the incorporation of $^3$H-thymidine into newly synthesized DNA. The APCs do not incorporate $^3$H-thymidine because they have been irradiated. Alternative methods for assessing proliferation that do not use radioisotopes are also known.

T cell response can also be determined by determining if one or more cytokines is released by the T cells. For this assay, APCs and the test vaccine composition are mixed and cultured. Either simultaneously or after a period of time sufficient for uptake and processing of an antigen within the vaccine composition by the APCs, T cells are added to the culture. After a period of time sufficient to allow activation of the T cells, growth of the culture is stopped, for example, by freezing. Freezing the culture lyses the cells and releases cytokines that have not yet been secreted into the culture medium. The presence or absence of cytokine in the culture medium can then be determined using known methods. Optionally, the amount of one or more cytokines in the culture medium can be determined. For example, cytokines in the culture supernatant and the cells can be measured using a bioassay, in which cell lines that proliferate only when stimulated with a particular cytokine (indicator cells) are cultured in media that is supplemented with an aliquot of the cytokine-containing culture media. The culture is maintained, typically, for 10–18 hours and $^3$H-thymidine is added. After an additional 6–10 hours, new DNA synthesis is measured by determining the amount of $^3$H incorporated into the cellular DNA. Any cytokine which is produced by the T cells upon activation can be measured. Examples of cytokines which can be determined include interferon-γ and interleukin-2.

In another embodiment, cytokine production is measured using an enzyme-linked immunosorbent assay (ELISA), for example, using reagents which are commercially available as kits. In this assay, an immobilized antibody is used to specifically capture a particular cytokine from the cytokine containing culture supernatant. Unbound proteins are washed away, and the amount of bound cytokine is determined by binding a second, labeled, antibody to the captured cytokine. This assay is quantitative and more specific than bioassays. Alternatively, cytokine mRNA levels can be quantitated using the polymerase chain reaction. Cytokine production can also be determined by staining producer T cells with labeled antibodies specific for the cytokine.

In another embodiment, the T cells are CD8$^+$ T cells and the response is measured by determining whether the T cells lyse the APCs which have been treated with the test vaccine composition. In one embodiment, the APCs are transformed peripheral blood lymphocyte cell lines (B-LCL) which have been incubated with $^{51}$CrO$_4^{2-}$. The resulting $^{51}$Cr-labeled PBLs are thoroughly washed, incubated with the test vaccine composition and then exposed to the antigen-specific CD8$^+$ T cells. After incubating for a sufficient period of time for epitope presentation by the B-LCLs and T cell activation, the extent of $^{51}$Cr release into the culture medium is determined. The amount of $^{51}$Cr released correlates with the extent of lysis of the B-LCLs.

The production of a T cell response can, generally, be determined by comparing the result achieved with the vaccine composition to a suitable control, as is known in the art. For example, in the $^{51}$Cr release assay discussed above, the amount of 51Cr released when the B-LCLs are treated with the CD8+ T cells can be compared to the amount released when the B-LCLs are treated with vehicle alone, referred to as the background release. Significantly (measurably) greater $^{51}$Cr release in the presence of the T cells is indicative of a T cell response. In the cytokine production assay, cytokine production by the T cells in the presence of APCs treated with the vaccine composition can be compared to cytokine production by the T cells in the absence of APCs, or in the presence of untreated APCs. Greater cytokine production in the presence of treated APCs is indicative of a T cell response.

The test vaccine composition comprises one or more antigens or one or more nucleic acid molecules which encode one or more antigens. The vaccine composition can be any of the types of vaccine compositions which are known in the art. For example, the vaccine composition can comprise an attenuated pathogen, such as a weakened bacterial strain or virus, or a killed pathogen, such as a killed bacterial strain or a killed virus. The vaccine composition can also comprise a portion of a pathogen, for example, a viral coat or bacterial membrane. In another embodiment, the vaccine composition comprises one or more proteins derived from a pathogen, for example, a protein which has been purified or partially purified from the pathogen, or a recombinant protein produced by a recombinant organism which expresses a gene derived from the pathogen which encodes the protein. Examples of suitable host organisms for the production of recombinant peptides and proteins are known in the art and include E. coli. The vaccine composition can also include one or more fragments of a protein or proteins derived from pathogen. Such protein fragments include peptides which are synthesized or recombinantly produced.

In another embodiment, the test vaccine composition includes one or more proteins, or fragments thereof, which are produced by a particular type of tumor cell. Preferably, the protein is unique to the tumor cell, i.e., not present in or on healthy cells, or is expressed in greater quantity by the tumor cell than by healthy cells. The protein can be, for example, a protein found on the surface of the tumor cell. The protein(s) can be derived from the tumor cells, for example, isolated and purified or partially purified from cultured tumor cells. The tumor cell protein(s), or a fragment or fragments thereof, can also be produced recombinantly.

In another embodiment, the vaccine composition comprises a nucleic acid molecule which encodes a protein or a fragment thereof, derived from a pathogen or a tumor cell as discussed above. For example, the vaccine composition can comprise so-called "naked DNA". The nucleic acid molecule can also be contained within a suitable vector, such as a recombinant virus, such as vaccinia virus, adenovirus, orf virus, fowlpox virus, herpes virus, varicella virus, papilloma virus, SV40, retroviruses, baculovirus and poliomyelitis virus. The vector can also be a bacterium, such as salmonella, BCG or E. coli. The nucleic acid can also be present in a liposome or another suitable vector, such as are known in the art.

As discussed above, the present invention enables the rapid assessment and comparison of a large number of potential vaccine compositions. For any given disease or pathogen, for example, a variety of antigens can be assessed. For example, a set of vaccine compositions which each include different antigens or portions of antigens from a particular pathogen can be compared. Further, for a given antigen, set of antigens, or nucleic acid molecule encoding such antigen(s), a variety of formulations can be assessed. For example, a set of vaccine compositions including the same antigen or antigens, but different vectors, adjuvants, concentrations, vehicles or excipients can be compared to determine the conditions necessary for optimal efficacy.

The invention will now be further and specifically described in the following examples.

EXAMPLES

Materials and Methods

Viruses

Influenza A viruses A/Puerto Rico/8/34 (H1N1) and A/Japan/305/57 (H2N2) were obtained from the Division of Virology, Bureau of Biologics, Food and Drug Administration, Bethesda, Md. A/Johannesburg/94 (H3N2) was obtained from David Burt (Pasteur Merieux Connaught, Toronto, Ontario, Canada). Influenza A viruses were propagated in 10-day-old, embryonated chicken eggs. Infected allantoic fluids were harvested 2 days after infection, aliquoted, and stored at −80° C. until use. Recombinant vaccinia viruses containing the genes coding for influenza A viral proteins HA, NA, M1, M2, PB1, PB2, PA, NS1, and NS2 and the nucleoprotein(NP) were obtained from B. Moss. Each of these was derived from the A/PR/8/34 influenza A virus strain, except for NS1, which was derived from A/Udorn/72. They were constructed and propagated as previously described (Smith et al., *Virology* 160: 336–345 (1987)). A recombinant vaccinia virus which expressed segmented portions of the NP was obtained from J. Bennink and L. Eisenlohr.

Human PBMC

PBMC specimens were obtained from normal, healthy donors. Most of the donors whose PBMC were tested had convincing evidence of influenza A virus-specific CTL activity in bulk culture. PBMC were purified by Ficoll-Hypaque density gradient centrifugation (A. Boyam, *Scand. J. Clin. Lab. Invest.* 21: 77–89 (1968)). Cells were resuspended at $2\times10^7$/mL in RPMI 1640 with 20% fetal bovine serum (FBS) (Sigma) and 10% dimethyl sulfoxide and cryopreserved until use. The HLA alleles of donor 1 were A2.1, A11, B18, B27, Cw1, Cw7, DR1, DQw1, DQw3, DRw52, and DRw53. HLA typing was performed in the HLA typing laboratory at the University of Massachusetts Medical Center.

Bulk Cultures of PBMC

Responder PBMC were suspended at $10^6$/mL in AIM-V medium (Gibco BRL, Grand Island, N.Y.) containing 10% human AB serum (NABI, Boca Raton, Fla.), penicillin-streptomycin, glutamine, and HEPES in a 70-mL flask (Falcon). Stimulators were infected with A/PR/8/34 at a multiplicity of infection (MOI) of 15 for 1.5 h at 37° C. in 1 mL of phosphate-buffered saline containing 0.1% bovine serum albumin and then added to responders in a flask at a stimulator-responder ratio of 1:10. On day 7 of culture, cells were either cloned by limiting dilution as described below or restimulated with gamma-irradiated (3,000 rads) autologous PBMC infected with A/PR/8/34 at an MOI of 15 for 1.5 h in 1 mL of phosphate-buffered saline containing 0.1% bovine serum albumin, added at a stimulator-responder ration of 1:10 in fresh medium containing 10% human AB serum and 20 U of interleukin-2 (IL-2) (Collaborative Biomedical Products, Bedford, Mass.). Restimulated cells were either cloned by limiting dilution or assayed for cytolytic activity 7 days later.

CTL Clones

Influenza virus-specific CTL clones were established by using a limiting-dilution technique as previously described (Kurane et al., *J. Exp. Med.* 170: 763–775 (1989)). PBMC which had been stimulated in bulk culture for 7 or 14 days were collected and plated at a concentration of 3, 10, or 30 cells per well in 96-well round-bottom microtiter plates in 100 µL of AIM-V medium containing 10% FBS, 20 U of IL-2, a 1:1,000 dilution of anti-CD8 monoclonal antibody 12F6 (obtained from Johnson Wong), and $10^5$ gamma-irradiated allogeneic PBMC/well. On day 7, 50 µL of fresh medium with FBS (Sigma immunochemicals, St. Louis, Mo.) and IL-2 were added, and on day 14, fresh medium with $10^5$ gamma-irradiated allogeneic PBMC/well and a 1:1,000 dilution of the anti-CD8 monoclonal antibody were added. Growing cells were assayed for cytolytic activity on days 21 and 28. Cells from wells with influenza A virus-specific cytolytic activity were expanded to 48-well plates.

Preparation of Target Cells

Autologous lymphoblastoid cell lines (B-LCLs) were established by culturing with Epstein-Barr virus in 24-well plates as previously described (Green et al., *J. Virol.* 67: 5962–5967 (1993)). B-LCL were infected with recombinant vaccinia viruses at an MOI of 20:1 for 1.5 h at 37° C. The cells were then diluted in 1 mL of medium and further incubated for 12 to 16 h. Other B-LCL were infected with A/PR/8/34, A/Japan/305/57, or A/Johannesburg/94 in 1 mL of medium for 12 to 16 h. These infected target cells were labeled with 0.25 mCi of $^{51}$Cr for 60 min at 37° C. After four washes, the target cells were counted and diluted to $2\times10^4$/mL for use in the cytotoxicity assay. The partially HLA-matched allogeneic target cells used in the assays were B-LCL produced in our laboratory form the HLA-typed PBMC of unrelated donors or were obtained from the National Institute of General Medical Sciences Human Genetic Mutant Cell Repository or the American Society for Histocompatibility and Immunogenetics Cell Bank and Repository.

Cytotoxicity Assays

Cytotoxicity assays were performed with 96-well round-bottom plates. Effector cells in 100 µL of RPMI 1640 medium containing 10% FBS were added to $2\times10^5$ $^{51}$Cr-labeled target cells in 100 µL at an effector-to-target (E-T) ratio of 10:1. Plates were centrifuged at 200×g for 5 min and incubated for 4 to 5 h at 37° C. Supernatant fluids were harvested by using the supernatant collection system (Skatron Instruments, Sterling, Va.), and $^{51}$Cr content was measured in a gamma counter. Percent specific $^{51}$Cr release was calculated with the following formula: (cpm experimental release−cpm spontaneous release)/(cpm maximum release−cpm spontaneous release)×100. All assays were performed in triplicate, and the results were calculated from the average of the triplicate wells.

Example 1

In Vitro Evaluation of Influenza Vaccine Compositions

This Example was designed to evaluate whether proper formulation of an influenza virus comprising a formalin-inactivated detergent-disrupted virus can lead to a CD8$^+$ cytotoxic T cell response.

The HA-Specific CD8$^+$ cytotoxic T cell clone described in Example 1 was incubated with autologous B-LCL cells which had been treated with one of the following vaccine formulations:

1. live influenza virus (H1N1, A/PR/8134, A/Texas/91)

2. iscomatrix alone 3. formalin-inactivated A/Texas/H1N1 virus; and 4. formalin-inactivated A/Texas/H1N1 virus formulated with Iscoms.

The results are shown in Table 1, which provides cytolysis as a per cent of total APCs and the background $^{51}$Cr release. The data show that the CD8$^+$ clone recognized APC infected with live flu virus or a recombinant vaccinia virus. This CD8$^+$ CTL clone, however, did not lyse APC pulsed with the inactivated A/Texas/H1N1 virus unless it was formulated with an adjuvant carrier. Formulation with Iscoms enabled processing of the vaccine for CD8$^+$ CTL recognition.

TABLE 1

Per cent lysis of B-LCLs treated with vaccine formulations by HA-specific cytotoxic T cell clone

|  | PR/8 virus | A/Tx virus | Iscomatrix | A/Tx vaccine | A/Tx Flu-Iscoms |
|---|---|---|---|---|---|
| CD8+ clone | 36.1% | 19.5% | −3.5% | −2.2% | 86.9% |
| min/max | 12.8% | 12.1% | 17.4% | 41.3% | 44.6% |

Example 2

In Vitro Evaluation of Recombinant Protein Vaccine Formulations

A human CD8+ cytotoxic T cell clone that recognizes amino acids 122–130 of the Influenza A NS1 protein is disclosed in U.S. Pat. No. 5,766,601, the teachings of which are incorporated herein by reference in their entirety. This T cell clone was incubated with autologous $^{51}$Cr-labeled B-LCL treated with (1) a synthetic peptide based on NS1 (aa 122–130); (2) recombinant NS1 protein; or (3) recombinant NS1 protein formulated as an Iscom. Controls were also established using uninfected B-LCL and B-LCL incubated with Iscoms only.

The results of this study are presented in Table 2. The CD8+ cytoxic T cell clone lysed APC that were treated with the recombinant NS1 aa 122–130 peptide and the recombinant NS1 protein/Iscom formulations. The CTL clone did not lyse APC treated with the recombinant protein alone or either of the control cells.

TABLE 2

Per cent lysis of autologous B-LCL treated with the indicated formulations by autologous NS1 aa 122–130 specific CD8+ cytotoxic T cell clone

|  | uninfected | NS1 aa 122–130 a | NS1 | NS1 protein Iscom b,c | Iscom d |
|---|---|---|---|---|---|
| CD8+ clone | −6.2% | 88.4 | −0.7% | 19.6% | −11.0 |
| min/max | 17.8% | 19.6 | −17.3% | 29.9% | 21.3% | a Peptide used at 25 μg/mL;
b Protein used at 35 μg/mL;
c Saponin used at 100 μg/mL;
d Saponin used at 70 μg/mL

Example 3

In vitro Evaluation of HIV-1 Vaccine Compositions

A human HIV-1 specific CD8+ cytotoxic T cell clone was prepared as described by Littaua et al., J. Virol. 65: 4051–4056 (1991), the teachings of which are hereby incorporated by reference in their entirety. The ability of this clone to recognize autologous APCs pulsed with (1) recombinant HIV-1 p24 protein alone; (2) HIV-1 p24 in an Iscom formulation; or (3) a recombinant vaccinia virus containing the HIV-1 p24 gene was determined.

The results are presented in Table 3, which shows that APCs treated with the recombinant vaccinia virus are significantly lysed by the T cell clone. APCs treated with the p24/Iscoms complex are also recognized by the T cell clone, but to a lesser extent. The T cell clone did not recognize B-LCLs pulsed with the recombinant p24 protein alone.

TABLE 3

Lysis of B-LCL treated with indicated formulations by human HIV-1 specific CD8+ cytotoxic T cell clone

|  | Iscoms + p24 at | | | Iscom | |
|---|---|---|---|---|---|
| Vac/p24 | 100 μg | 50 μg | 25 μg | 100 μg | Media |
| 37.5 | 11.4 | 20.2 | −0.1 | −2.6 | 0.3 |

Example 5

In vivo Evaluation of Influenza Virus Compositions

Fifty-five healthy adults from 18 to 45 years old were enrolled in 5 study groups of 11 participants each: 1. Fluzone; 2. Flu-Iscom (75 μg); 3. Flu-Iscom (50 μg); 4. Flu-Iscomatrix (75 μg); and 5. Flu-Iscomatrix (50 μg). Cytotoxic T cell activity in the peripheral blood lymphocytes of the subjects was determined on days 0, 14 and 56 following a single immunization with trivalent vaccine. Peripheral blood lymphocytes at each time point for each subject were tested in the same assay for killing of virus-infected autologous target cells (Epstein-Barr virus transformed B cells) at various E:T ratios (90, 30 and 10). Responders were those subjects which showed a significant increase in killing of greater than 5% compared with the percent net lysis at time 0 at two or more effector:target ratios. The results are presented in Table 4.

TABLE 4

| Virus Strain | Fluzone alone 50/45 | Flu-Iscom 75/45 | Flu-Iscom 50/45 | Flu MTRX 75/45 | Flu MTRX 50/45 |
|---|---|---|---|---|---|
| H1 | 0/11 | 7/11 | 5/11 | 1/11 | 5/11 |
| H3 | 1/11 | 3/11 | 7/11 | 3/11 | 5/11 |
| B | 5/11 | 6/11 | 5/11 | 6/11 | 7/11 |

Figure 1B:
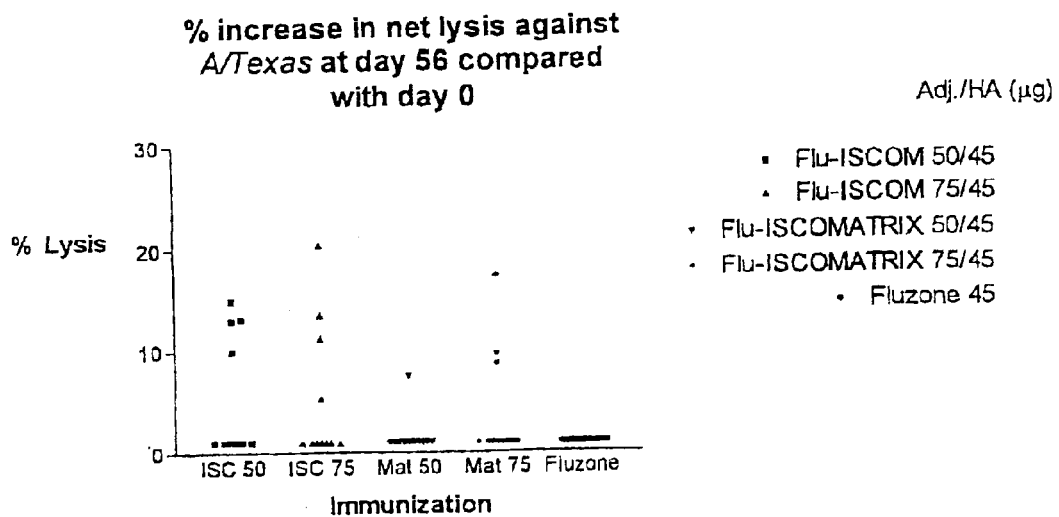
FIG. 1B is a graph showing the increase in percent lysis against influenza virus strain A/Texas compared to day 0 for several fluzone formulations at day 56.
Figure 2A:
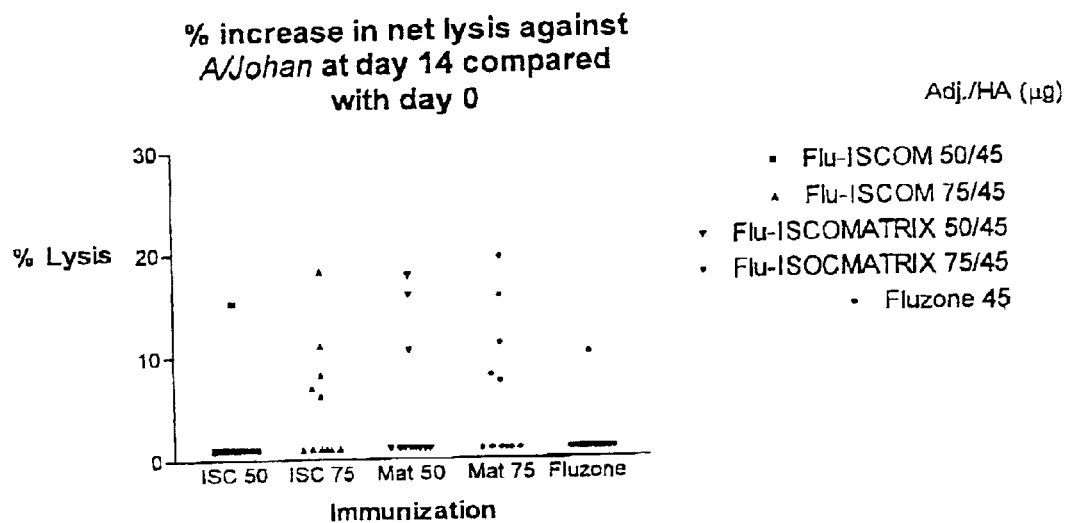
FIG. 2A is a graph showing the increase in percent lysis against influenza virus strain A/Johannesburg compared to day 0 for several fluzone formulations at day 14.
Figure 2B:
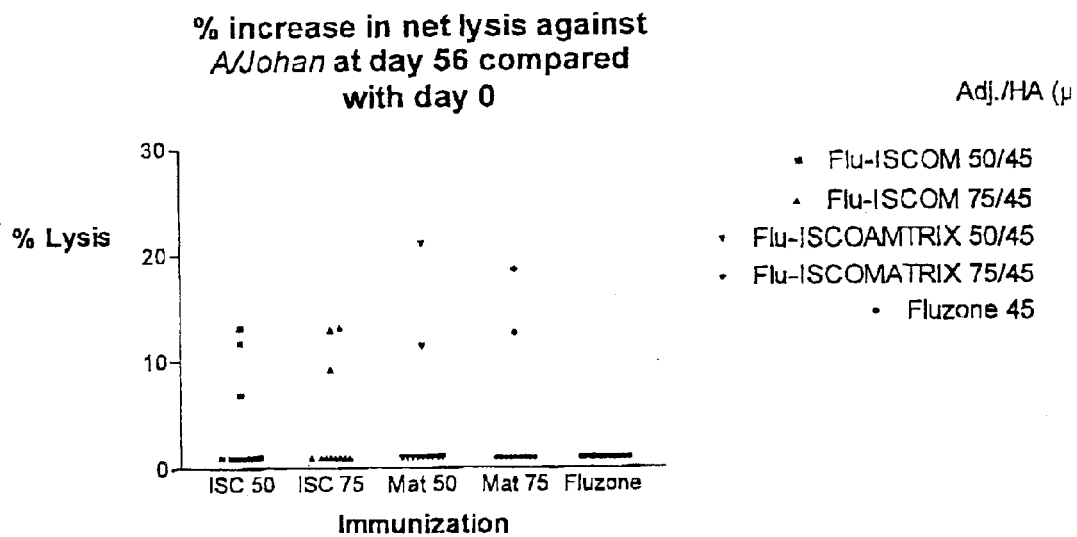
FIG. 2B is a graph showing the increase in percent lysis against influenza virus strain A/Johannesburg compared to day 0 for several fluzone formulations at day 56.

These results show that the effect of the adjuvant was significant for virus strains H1 and H3, while results were similar for strain B in the presence and absence of an adjuvant. FIGS. 1A and 1B also present data illustrating the increase in net lysis compared to day 0 for strain A/Texas at days 14 and 56, respectively. Similar data for strain A/Johannesburg are illustrated in FIGS. 2A and 2B.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for selecting one or more vaccine compositions from among a group consisting of two or more distinct vaccine compositions for assessment in one or more human subjects, said vaccine compositions each comprising one or more nucleic acid molecules encoding one or more antigens which comprise the same CD8+ T cell epitope, said method comprising the steps of:

(a) contacting human antigen presenting cells in culture with a vaccine composition selected from among said group of vaccine compositions, thereby, if one or more of the nucleic acid molecules encoding one or more antigens which comprise said T cell epitope are taken up and processed by said antigen presenting cells, producing one or more processed antigens;

(b) contacting said antigen presenting cells of step (a) with monoclonal human T cells, wherein the monoclonal human T cells, are CD8$^+$ T cells, under conditions sufficient for said T cells to respond to one or more of the processed antigens;

(c) determining the level of said T cells' response to one or more of the processed antigens;

(d) repeating steps (a), (b) and (c) with each additional vaccine composition in the group; and (e) selecting at least one vaccine composition that exceeds a predetermined level of said T cells' response for assessment in one or more human subjects.

2. The method of claim 1 wherein the human antigen presenting cells are autologous cells with the monoclonal T cells.

3. The method of claim 1 wherein the human antigen presenting cells are selected from the group consisting of macrophages, dendritic cells and B cells.

4. The method of claim 1 wherein the level of T cells' response to the processed antigen is indicated by the level of release of one or more cytokines or level of lysis of the antigen presenting cells.

5. The method of claim 1 wherein steps (a) and (b) are conducted simultaneously.

6. The method of claim 1 wherein the one or more vaccine compositions further comprise an immunostimulating complex.

7. A method for optimizing the T cell response against a T cell epitope comprising the steps of:

(a) separately contacting human antigen presenting cells in culture with each of two or more distinct vaccine compositions, wherein each of the distinct vaccine compositions comprises one or more nucleic acid molecules encoding one or more antigens which comprise the same specific T cell epitope, under conditions suitable for said human antigen presenting cells to take up nucleic acid molecules and permit the human antigen presenting cells to produce one or more processed antigens;

(b) contacting the antigen presenting cells produced by step (a) with monoclonal human T cells having a T cell receptor specific for said specific T cell epitope and known HLA allele for said T cells under conditions sufficient for said T cells to respond to the processed antigen;

(c) determining the T cell response to the processed antigen of each distinct vaccine composition, whereby the vaccine composition possessing an optimal response is selected; and (d) assessing the vaccine composition selected in step (c) in one or more human subjects.

8. The method of claim 7 wherein the monoclonal human T cells are CD4$^+$ T cells and the T cell epitope is a CD4 epitope.

9. The method of claim 7 wherein the monoclonal human T cells are CD8$^+$ T cells and the T cell epitope is a CD8 epitope.

10. The method of claim 7 wherein the human antigen presenting cells are selected from the group consisting of macrophages, dendritic cells and B cells.

11. The method of claim 7 wherein the T cell response to the processed antigen is indicated by the level of release of one or more cytokines or level of lysis of the antigen presenting cells.

12. The method of claim 7 wherein the T cell response to the processed antigen is indicated by the level of release of one or more cytokines or the level of stimulated formation of antibodies by B cells.

13. The method of claim 7 wherein steps (a) and (b) are conducted simultaneously.

14. The method of claim 7 wherein the vaccine compositions further comprise an immunostimulating complex.

15. The method of claim 7 wherein the human antigen presenting cells are autologous cells with the monoclonal T cells.

16. A method for selecting one or more vaccine compositions from among a group consisting of two or more distinct vaccine compositions for assessment in one or more human subjects, said vaccine compositions each comprising one or more nucleic acid molecules encoding one or more antigens which comprise the same CD4$^+$ T cell epitope, said method comprising the steps of:

(a) contacting human antigen presenting cells in culture with a vaccine composition selected from among said group of vaccine compositions, thereby, if one or more of the nucleic acid molecules encoding one or more antigens which comprise said T cell epitope are taken up and processed by said antigen presenting cells, producing one or more processed antigens;

(b) contacting said antigen presenting cells of step (a) with monoclonal human T cells, wherein the monoclonal human T cells, are CD4$^+$ T cells, under conditions sufficient for said T cells to respond to one or more of the processed antigens;

(c) determining the level of said T cells' response to one or more of the processed antigens;

(d) repeating steps (a), (b) and (c) with each additional vaccine composition in the group; and (e) selecting at least one vaccine composition that exceeds a predetermined level of said T cells' response for assessment in one or more human subjects.

17. The method of claim 16 wherein the human antigen presenting cells are autologous cells with the monoclonal T cells.

18. The method of claim 16 wherein the human antigen presenting cells are selected from the group consisting of macrophages, dendritic cells and B cells.

19. The method of claim 16 wherein the level of T cells' response to the processed antigen is indicated by the level of release of one or more cytokines or the level of stimulated formation of antibodies by B cells.

20. The method of claim 16 wherein steps (a) and (b) are conducted simultaneously.

21. The method of claim 16 wherein the one or more vaccine compositions further comprise an immunostimulating complex.

* * * * *